(12) United States Patent
Engel et al.

(10) Patent No.: US 10,429,303 B2
(45) Date of Patent: Oct. 1, 2019

(54) PORTABLE AND AUTONOMOUS, IOT ENABLED, OPTICAL MEASUREMENT SYSTEM

(71) Applicant: INTERNATIONAL BUSINESS MACHINES CORPORATION, Armonk, NY (US)

(72) Inventors: Michael Engel, Rio de Janeiro (BR); Jeannette M. Garcia, San Leandro, CA (US); Ricardo L. Ohta, Sao Paulo (BR); Ademir F. Silva, Sao Paulo (BR); Mathias B. Steiner, Rio de Janeiro (BR); Jaione Tirapu Azpiroz, Rio de Janeiro (BR); Thomas G. Zimmerman, Cupertino, CA (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 158 days.

(21) Appl. No.: 15/469,007

(22) Filed: Mar. 24, 2017

(65) Prior Publication Data

US 2018/0275056 A1    Sep. 27, 2018

(51) Int. Cl.
*G01N 21/64* (2006.01)
*G01V 8/12* (2006.01)
(Continued)

(52) U.S. Cl.
CPC ......... *G01N 21/645* (2013.01); *G01N 21/643* (2013.01); *G01N 21/6452* (2013.01);
(Continued)

(58) Field of Classification Search
CPC ......... G01N 2021/6482; G01N 21/645; G01N 2201/061; G01N 2201/12; G01V 8/12
See application file for complete search history.

(56) References Cited

U.S. PATENT DOCUMENTS

| | | | | |
|---|---|---|---|---|
| 6,104,484 A | * | 8/2000 | Nagata | G01N 21/553 356/246 |
| 2002/0045272 A1 | * | 4/2002 | McDevitt | B01L 3/0289 436/518 |

(Continued)

OTHER PUBLICATIONS

Sarojam, Praveen, "Analysis of Trace Metals in Drinking Water with the Optima 7000 DV ICP-OES", ICP—Optical Emission Spectroscopy, PerkinElmer, Inc., Oct. 2011, 5 pages.

(Continued)

*Primary Examiner* — Marcus H Taningco
(74) *Attorney, Agent, or Firm* — Tutunjian & Bitetto, P.C.; Vazken Alexanian

(57) ABSTRACT

A portable optical measurement system is provided for performing metal trace analysis on a liquid sample. The system includes a sample holder for holding an analysis substrate that includes the liquid sample during the metal trace analysis. The system further includes an ultraviolet (UV) light source for emitting ultraviolet light illuminating the liquid sample. The system also includes an optical sensor for detecting radiation emanating from the liquid sample and converting the detected radiation into an electrical signal. The system additionally includes a microcontroller for processing the electrical signal. The system further includes an external interface for transmitting the processed electrical signal to an external device.

17 Claims, 14 Drawing Sheets

(51) Int. Cl.
  *G01N 21/01* (2006.01)
  *G01N 21/77* (2006.01)
(52) U.S. Cl.
  CPC ............... *G01N 2021/0118* (2013.01); *G01N 2021/7793* (2013.01); *G01N 2201/0221* (2013.01)

(56) References Cited

U.S. PATENT DOCUMENTS

| | | | |
|---|---|---|---|
| 2004/0092025 A1* | 5/2004 | Mordekhay | G01N 35/00029 436/55 |
| 2006/0198761 A1* | 9/2006 | Tokhtuev | G01N 21/251 422/82.05 |
| 2010/0061885 A1* | 3/2010 | Harley | G01N 21/85 422/3 |
| 2012/0257193 A1* | 10/2012 | Hummel | B01F 13/0066 356/73.1 |
| 2015/0355090 A1 | 12/2015 | Boday et al. | |
| 2015/0355156 A1 | 12/2015 | Boday et al. | |
| 2016/0018339 A1* | 1/2016 | Perkins | G01N 33/1833 73/61.48 |
| 2018/0335390 A1* | 11/2018 | Leung | G01N 21/6428 |

OTHER PUBLICATIONS

Seal Analytical, Water Analyzer, http://seal-analytical.com/Markets/WaterAnalysis, last downloaded Dec. 30, 2016, 2 pages.

Wojtecki, et al., "Development of a Method for Detecting Trace Metals in Aqueous Solutions Based on the Coordination Chemistry of Hexahydrotriazines", https://www.ncbi.nlm.nih.gov/pubmed/26035633, Aug. 2015, 2 pages.

* cited by examiner

PORTABLE AND AUTONOMOUS, IOT ENABLED, OPTICAL MEASUREMENT SYSTEM

BACKGROUND

Technical Field

The present invention relates generally to information processing and, in particular, to a portable and autonomous, Internet of Things (IoT) enabled, optical measurement system.

Description of the Related Art

Heavy metal traces found in drinking and irrigation water sources can end up contaminating the food chain and pose serious threats to human health, especially for heavy metals such as lead, even at low concentration. Hence, there is, a need for frequent monitoring of water supplies, from rivers and creeks to public and private drinking water systems.

SUMMARY

According to an aspect of the present invention, a portable optical measurement system is provided for performing metal trace analysis on a liquid sample. The system includes a sample holder for holding an analysis substrate that includes the liquid sample during the metal trace analysis. The system further includes an ultraviolet (UV) light source for emitting ultraviolet light illuminating the liquid sample. The system also includes an optical sensor for detecting radiation emanating from the liquid sample and converting the detected radiation into an electrical signal. The system additionally includes a microcontroller for processing the electrical signal. The system further includes an external interface for transmitting the processed electrical signal to an external device.

According to another aspect of the present invention, a portable optical measurement system is provided for performing metal trace analysis on a liquid sample. The system includes a sample holder for holding an analysis substrate that includes a metal detection material and fluorescent markers, deposited over a UV transparent substrate, for receiving the liquid sample during the metal trace analysis. The system further includes an ultraviolet (UV) light source for emitting ultraviolet light illuminating the liquid sample. The system also includes an optical sensor for detecting radiation emanating from the liquid sample and converting the detected radiation into an electrical signal. The system additionally includes a microcontroller for processing the electrical signal. The system further includes an external interface for transmitting the processed electrical signal to an external device to determine a presence or an absence of a metal trace in the liquid sample. The system also includes a communication indicator for receiving a communicated signal from the external device that indicates a status representative of the presence or the absence of the metal trace in the liquid sample, and for indicating the status to a user.

These and other features and advantages will become apparent from the following detailed description of illustrative embodiments thereof, which is to be read in connection with the accompanying drawings.

BRIEF DESCRIPTION OF THE DRAWINGS

The following description will provide details of preferred embodiments with reference to the following figures wherein.

DETAILED DESCRIPTION

The present invention is directed to a portable and autonomous, Internet of Things (IoT) enabled, optical measurement system.

In an embodiment, the present invention provides a portable optical measurement module that supports liquid sample analysis, can be used in the field and also supports cloud connectivity.

In an embodiment, the present invention provides a customized optical measurement module that supports UV-C (Ultra Violet range between 100 nm-280 nm) light illumination and fluorescence emission detection, which is compatible with metal trace analysis present in liquid samples and, in addition, is portable to enable use in the field further supporting cloud connectivity.

Figure 1:
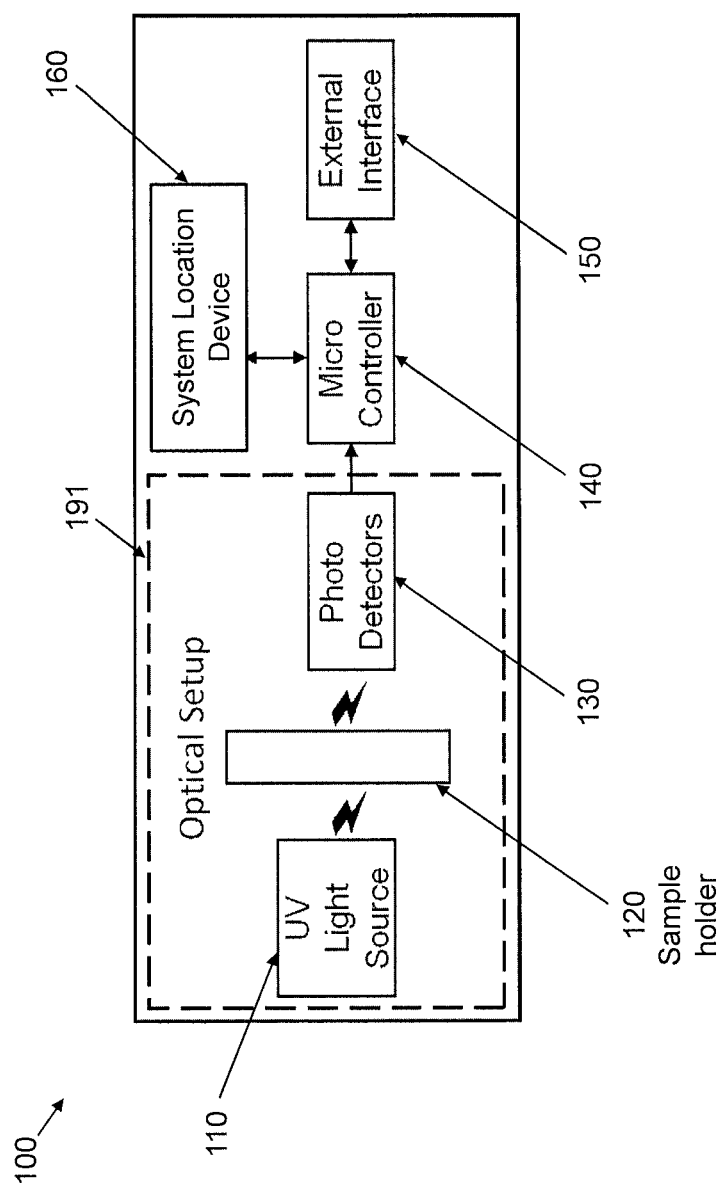
FIG. 1 shows the block diagram of an exemplary system for portable and autonomous, IoT enabled, optical measurement, in accordance with an embodiment of the present invention.

FIG. 1 shows an exemplary system 100 for portable and autonomous, IoT enabled, optical measurement, in accordance with an embodiment of the present invention.

The system 100 includes asp ultraviolet (UV) light source 110, a sample holder 120, a set of one or more photodetectors 130, a microcontroller 140, an external interface 150, and a system location device 160.

The UV light source 110, the sample holder 120, and the set of one or more photodetectors 130 are collectively referred to herein as "sensor" 191. The UV light source 110, the sample holder 120, the set of photodetectors 130, the microcontroller 140, the external interface 150, and the system location device 160 can be collectively referred to as "measurement module" 400 when a casing is added, such as the casing shown in FIG. 4. For the sake of illustration and clarity, one sensor 191 is shown. However, in other embodiments, system 100 can include multiple sensors, while maintaining the spirit of the present invention.

The UV light source 110 provides UV light that is then used to analyze a liquid under investigation (hereinafter interchangeably referred to as "liquid sample"), in an embodiment, the UV light source 110 outputs UV light having a wavelength of 255 nm. Alternatively, other wavelengths can be used, while maintaining the spirit of the present invention. In an embodiment, the UV light source 110 can be implemented by means of a PCB having one or more UV LEDs and a DC/DC voltage regulator. It is possible for the UV light source 110 and/or the PCB implementing the same to have additional elements as readily appreciated by one of ordinary skill in the art, while maintaining the spirit of the present invention.

The sample holder 120 holds the analysis substrate, which includes the liquid sample under analysis. In an embodiment, the analysis substrate includes a metal detection substance (e.g., hexahydrotriazine (HT) and/or hemiamminal (HA) and/or so forth) deposited over a fluorescent indicator. The metal detection substance absorbs UV light in response to the concentration of metal in the liquid sample under analysis. The fluorescent indicator receives the remainder of the UV light that is not absorbed by the metal detection substance and converts the UV light to a longer wavelength (i.e., wavelength of lower energy), which is detected by the photodetectors 130. The function of the fluorescent indicator is to shift the UV light wavelength to a wavelength within the sensitivity of the photodetectors 130. In another embodiment, photodetectors 130 that are sensitive to the UV light are used, enabling direct measurement of the UV light that passes through and is not absorbed by the metal detection substance, eliminating the need for a fluorescent indicator.

The set of photodetectors 130 are responsible to detect variations in fluorescence intensity due to the absorption of UV light by the metal detection substance in response to the presence of metal traces in the liquid sample, by converting light into an electrical signal (voltage/current). In an embodiment, the set of photodetectors 130 includes two photodetectors to perform a differential measurement, where one photodetector measures the UV absorbed produced by the liquid sample under analysis and the other measures the UV absorbed by the metal detection substance without any liquid, sample under analysis, the latter providing a control (i.e. "zero metal") reference signal. Of course, other numbers of photodetectors can also be used, while maintaining the spirit of the present invention.

The microcontroller 140 collects the output signals from the photodetectors 130 and performs pre-processing operations on the output signals from the photodetectors 130 (such as converting analog input signals to digital format and/or temporary data storage). Moreover, the microcontroller 140 performs excitation signal generation and control for the UV light source 110. The microcontroller 140 is interchangeably referred to herein as "µcontroller" and "computer".

The external interface 150 includes connection devices for interfacing with a visualization module and other external devices. The visualization module can be a device which includes a display and a user interface and which provides a visualization of the results of an analysis of the liquid sample regarding metal traces present in the liquid sample.

The system location device 160 provides or receives location information designating where the liquid sample was collected/analyzed. In an embodiment, the system location device 160 can include a Global Positioning System (GPS) device for providing the location information. In an embodiment, the system location information 160 can include a memory for receiving the location information from a user via the external interface 150. In an embodiment, the system location information 160 can include a memory and a user input for receiving the location information from a user.

Figure 2:
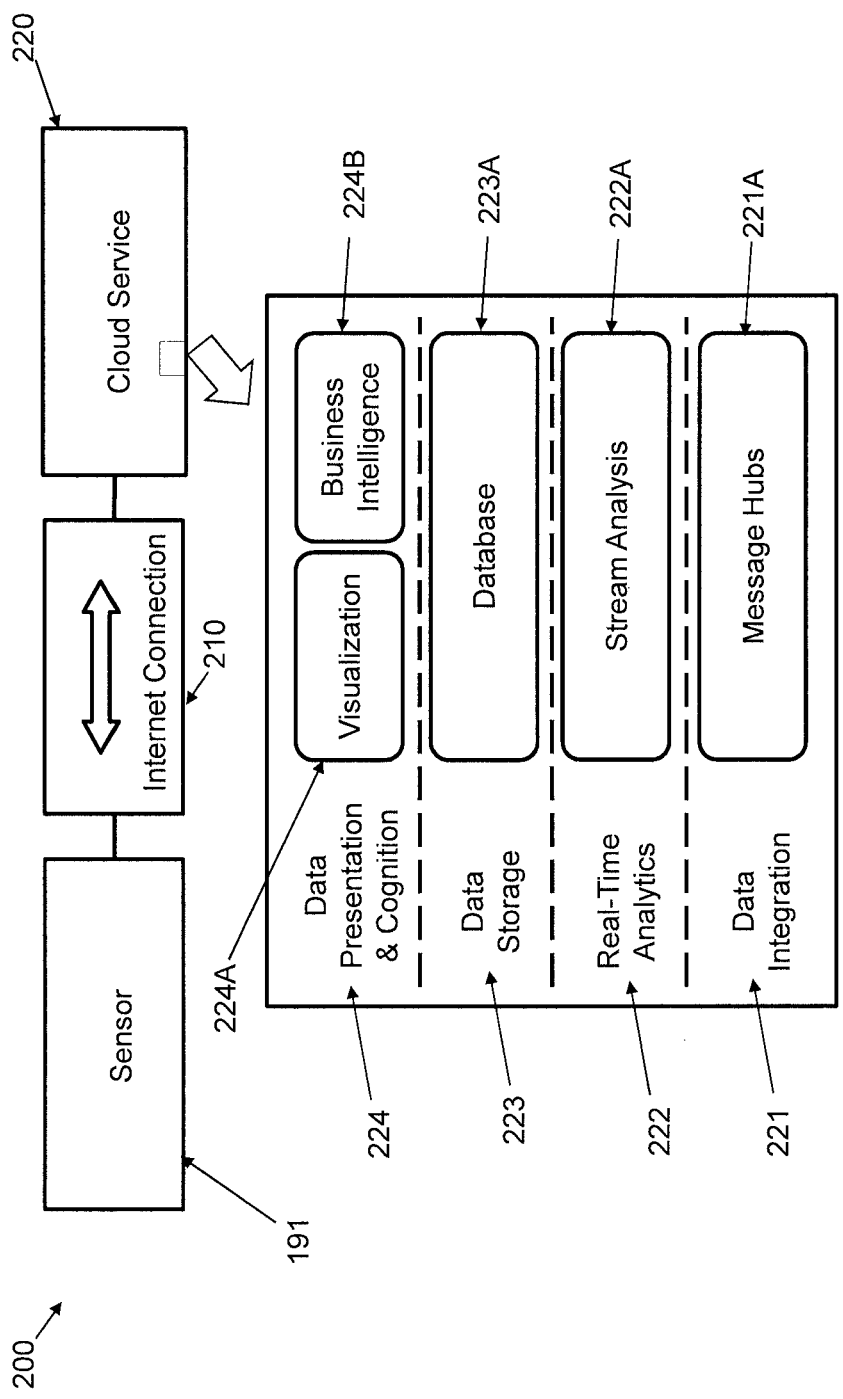
FIG. 2 shows connectivity diagram of the present invention and the Cloud Service components, in accordance with an embodiment of the present invention.

FIG. 2 shows connectivity diagram 200 of the present invention and the Cloud Service components, in accordance with an embodiment of the present invention.

The connectivity 200 involves sensor 191, a network (e.g., the Internet) connection 210, and a cloud service (application) 220.

The cloud service 220 includes a data integration layer 221, a real-time analytics layer 222, a data storage layer 223, and a data presentation and cognition layer 224.

The data integration layer 221 is an abstraction layer which performs the reception and transmission of metal trace data packets belonging to a sensor 191 of system 100. These data packets can be represented by text messages, images, other events, and so forth. In an embodiment, an implementation of this layer can use telemetry messaging protocols such as MQTT (Message Queuing Telemetry Transport). In such a case, the IBM® IoT Foundation cloud service can be used. Of course, other protocols can be used, while maintaining the spirit of the present invention. In an embodiment, the data integration layer 221 includes message hubs 221A.

The real-time analytics layer 222 can be used to treat some messages received from sensors with specific and predefined actions. For instance, this system may reply with a message, to the respective sensor device to trigger an indicator (e.g., but not limited to, a Light Emitting Diode (LED), a speaker, etc.) warning, that the data is above a normal value, considering other similar sensors and, thus, requires operator attention or some automated action (e.g., but not limited to, turn off LED, shut down the system, etc.). In an embodiment, the real-time analytics layer 222 includes a stream analyzer 222A for performing the preceding functions.

The data storage layer 223 provides data persistence using a database 223A. Among the different forms of implementation are cloud services that store and organize data in structured (SQL—Structured Query Language) or unstructured way (NoSQL). Examples include IBM® DB2, Cloudant®, MongoDB®, and so forth, The data presentation and cognition layer 224 provides visualization of data gathering by web applications, firmware updates, data queries adapted to mobile applications, statistics and/or visual trends of data interpretations, and automated cognitive insights. In an embodiment, the data presentation and cognition layer 224 includes a visualizer 224A and a business intelligence module 224B for performing the preceding functions.

Figure 3:
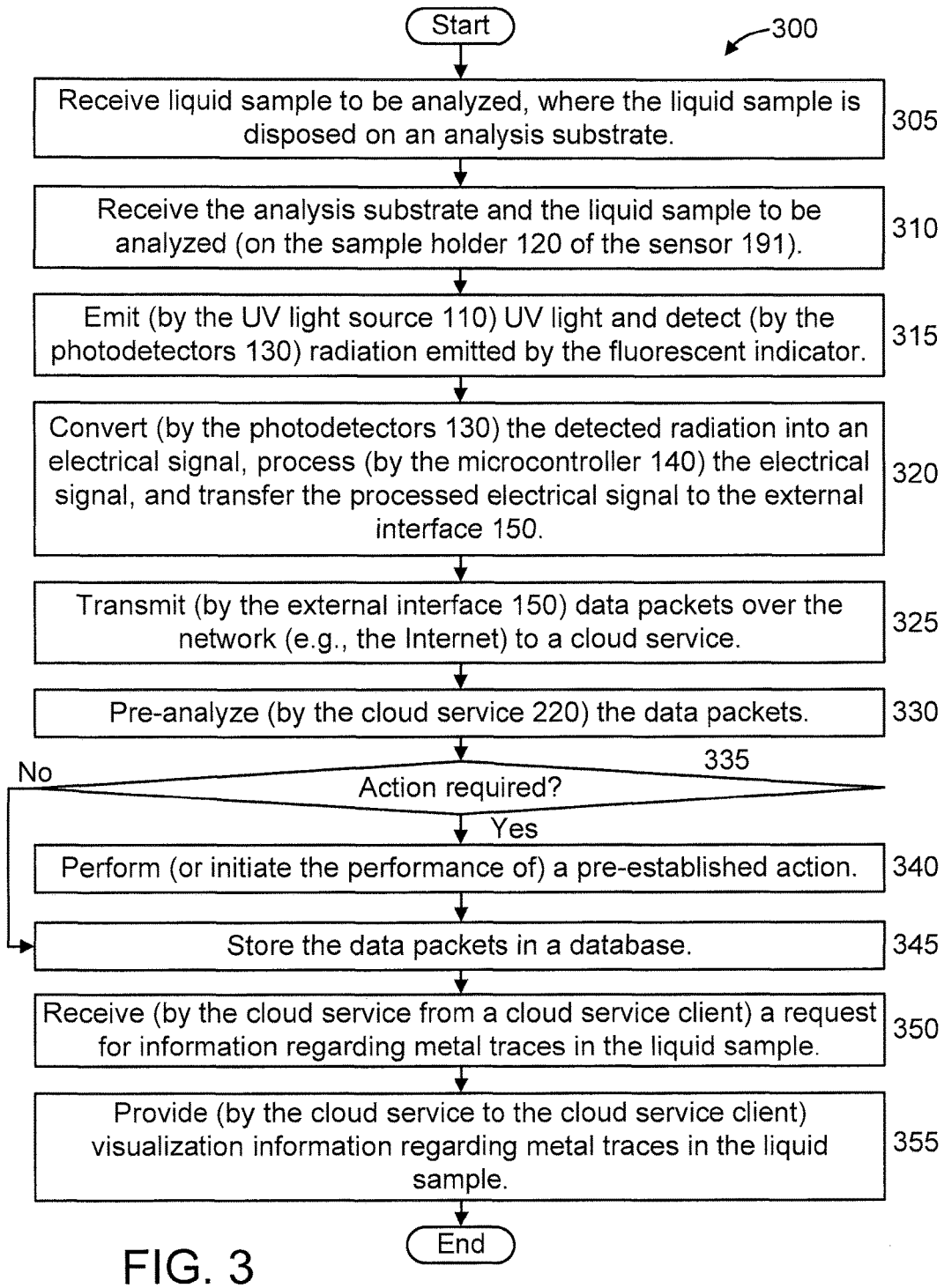
FIG. 3 shows an exemplary method for performing portable and autonomous, IoT enabled, optical measurements, in accordance with an embodiment of the present invention.

FIG. 3 shows an exemplary method 300 for performing portable and autonomous, IoT enabled, optical measurements, in accordance with an embodiment of the present invention.

At step 305, receive liquid sample to be analyzed, where the liquid sample is disposed on an analysis substrate.

At step 310, receive the analysis substrate and the liquid sample to be analyzed (on the sample holder 120 of the sensor 191).

At step 315, emit (by the UV light source 110) UV light and detect (by the photodetectors 130) radiation emitted by the fluorescent indicator, under influence of the UV light that passes through (and is not absorbed by) the metal detection substance, in response to the trace metal concentration present in the liquid sample.

At step 320, convert (by the photodetectors 130) the detected radiation into an electrical signal, process (by the microcontroller 140) the electrical signal, and transfer the processed electrical signal to the external interface 150.

At step 325, transmit (by the external interface 150) data packets over the network (e.g., the Internet) to a cloud service.

At step 330, pre-analyze (by the cloud service 220) the data packets.

At step 335, determine whether a specific action is required, based on a result of the pre-analysis performed by step 330. If so, then continue to step 340. Otherwise, continue to step 345.

At step 340, perform (or initiate the performance of; a pre-established action. The particular action that is performed can be selected from a set of pre-established actions, where the particular selection is based on the result of the pre-analysis performed by step 330.

At step 345, store the data packets in a database.

At step 350, receive (by the cloud service from a cloud service client) a request for information regarding metal traces in the liquid sample.

At step 355, provide (by the cloud service to the cloud service client) visualization information regarding metal traces in the liquid sample.

Figure 4:
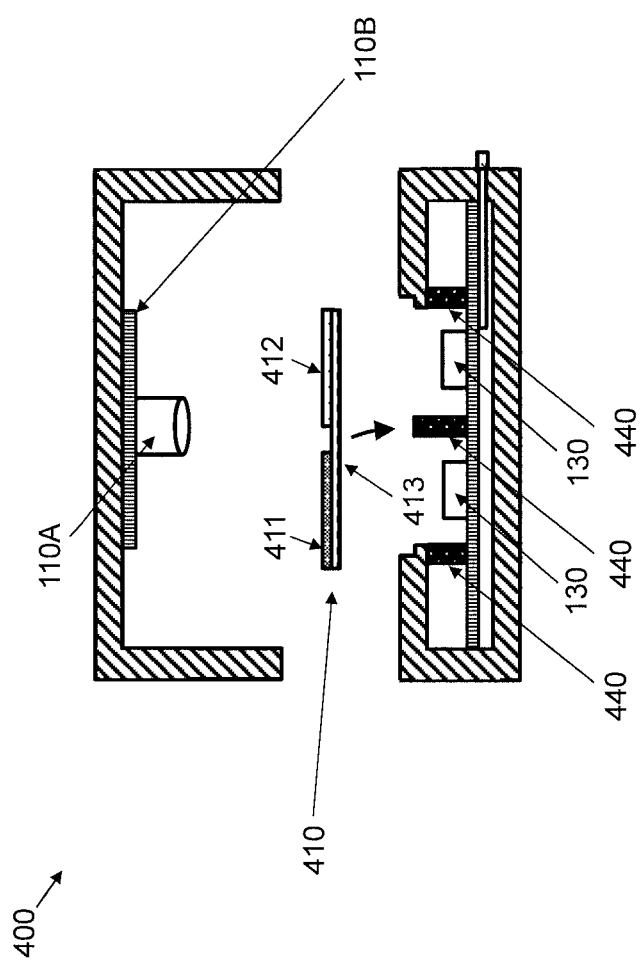
FIG. 4 shows a partially exploded view of a frontal cross-sectional schematic view of a measurement 400, in accordance with an embodiment of the present invention.
Figure 5:
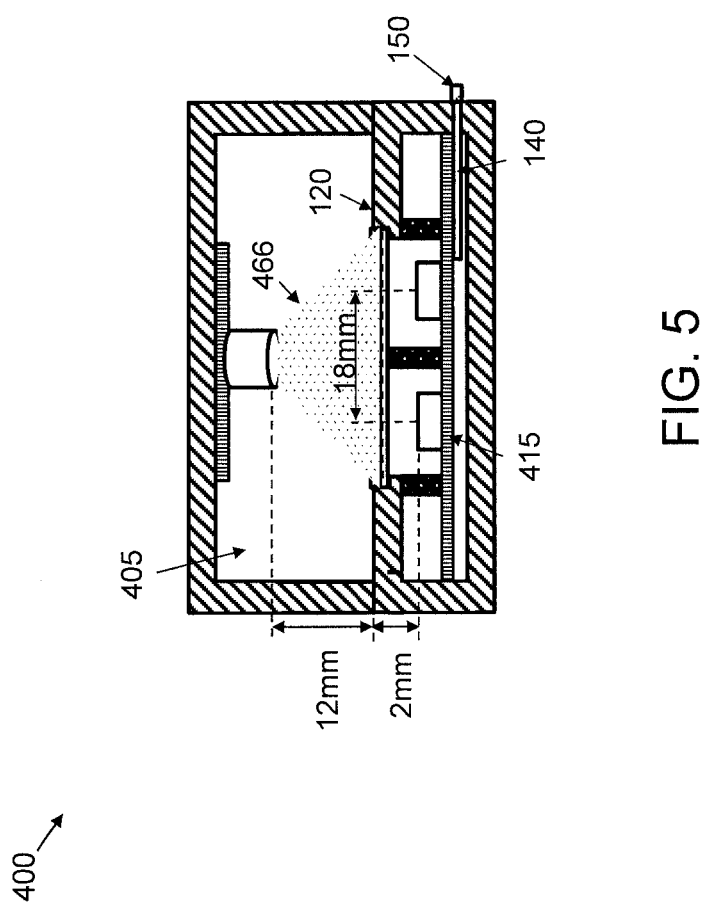
FIG. 5 shows a (non-exploded) view of a frontal cross-sectional schematic view of the measurement module of FIG. 4 with the sample inside the measurement module 400, executing an analysis, in accordance with an embodiment of the present invention.
Figure 6:
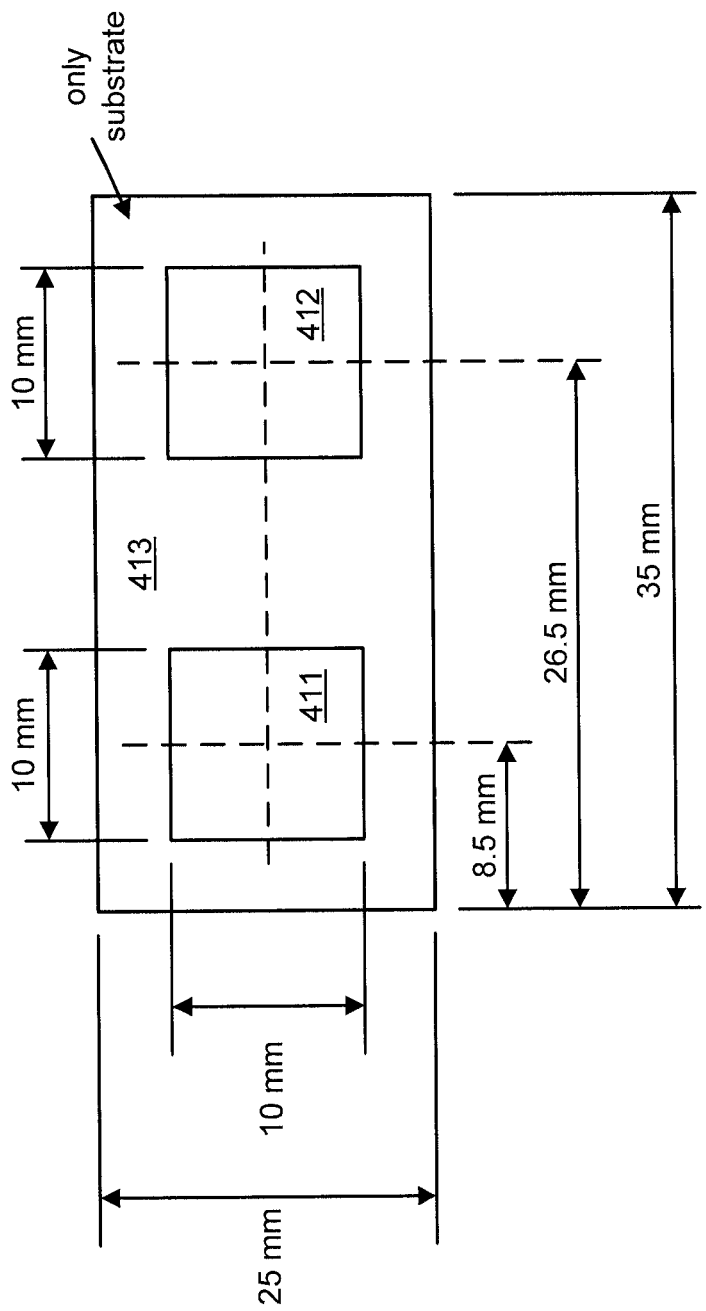
FIG. 6 further shows the analysis substrate dimensions, in accordance with an embodiment of the present invention.

FIG. 4 shows a partially exploded front cross-sectional view of a schematic of a measurement module 400, in accordance with an embodiment of the present invention. FIG. 5 shows a (non-exploded front cross-sectional) view of the schematic of the measurement module 400 of FIG. 4, executing sample analysis, in accordance with an embodiment of the present invention. FIG. 6 further shows the exemplary dimensions of the analysis substrate, in accordance with an, embodiment of the present invention. It is to be appreciated that any dimensions provided herein are so provided for the sake of illustration. Hence, as readily appreciated by one of ordinary skill in the art, other dimensions can also be used, while maintaining the spirit of the present invention.

The measurement module 400 includes an optical setup within a dark measurement chamber 405 that includes a UV light source e.g., an LED diode 110A and a PCB 110B) 110 for illuminating (by a UV light 466) an analysis substrate 410 and two photodetectors 130 placed in parallel for measuring the light emanating from the other side of both a test/wetted area (hereinafter "test area" or "test region") 411 and a reference/baseline area (hereinafter "reference area" or "reference region") 412 of the analysis substrate 410, respectively.

The analysis substrate 410 including the liquid sample is placed on the movable sample holder 120 that slides into the dark measurement chamber 405.

The measurement module 100 also includes the microcontroller 140, a custom PCB 415 for electrical circuitry, and the external interface 150. In an embodiment, the external interface 150 includes two connection devices for connection to and compatibility with a visualization device and/or other external peripherals or computing devices. Of course, other numbers of connection devices can be included. The connection devices can be, for example, but are not limited to, connectors, network (e.g., but not limited to, Ethernet, Wifi, etc.) adapters, and so forth. In addition, any wireless communication technology/protocol can be used by the connection devices including, but not limited to, Zigbee®, WiFi, 3G, 4G, Bluetooth®, and so forth.

The microcontroller 140 is used for excitation signal generation and control, including excitation signal generation and control for the UV light source 110, as well as collection and processing of the measurement data.

The measurement module 400 further includes external light blockers 440.

As noted above, the analysis substrate 410 includes a wetted test area 411 and a reference area 412. The test area 411 and the reference area 412 are disposed on a UV transparent substrate 413 of the analysis substrate 410.

Referring to FIG. 6, an exemplary UV transparent substrate 413 can have a size of 25 mm by 35 mm, with the test area 411 having a size of 10 mm by 10 mm, and the reference area 412 having a size of 10 mm by 10 mm. A centerline through the test area 411 is disposed 8.5 mm from a left side/edge of the UV transparent substrate 413, while a centerline through the reference area 412 is disposed 26.5 mm from the left side edge of the UV transparent substrate 413. However, as noted above, dimensions are provided herein for illustrative purposes and, thus, other dimensions and layout can be used, depending upon the implementation, while maintaining the spirit of the present invention, FIG. 7 shows another partially exploded view of some of the elements of the measurement module 400 of FIG. 4, in accordance with an embodiment of the present invention.

Figure 7:
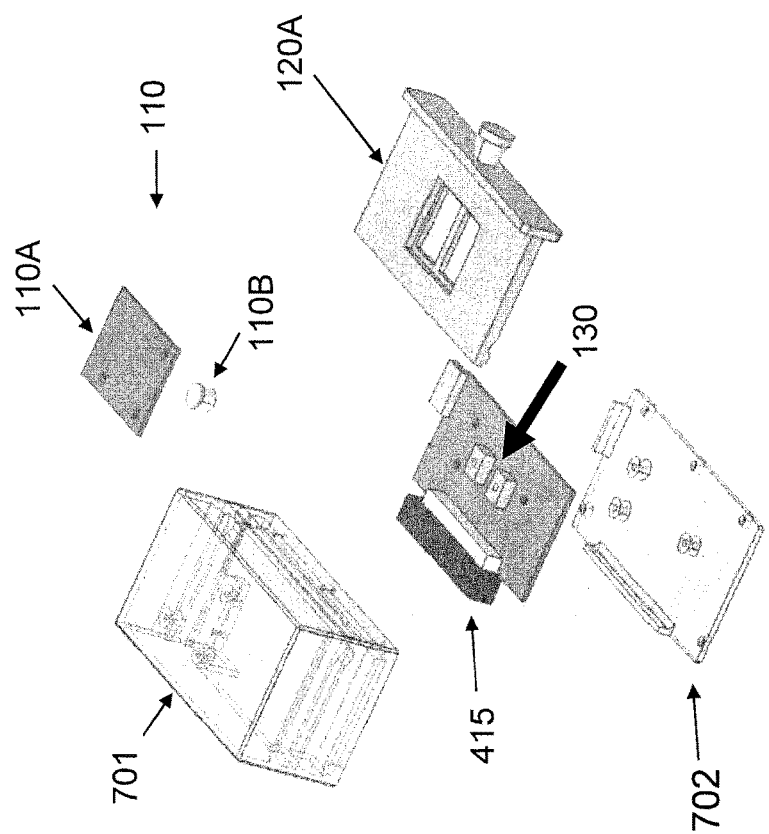
FIG. 7 shows another partially exploded view of some of the elements of the measurement module of FIG. 4, in accordance with an embodiment of the present invention.

The measurement module 400 includes a case 701, a bottom cover 702, the UV light source 110 (implemented at least in part in the example of FIG. 7 by a PCB 110A having a UV LED 1101 disposed thereon), the PCB 415 (having the microcontroller 140 and the photodetectors 130 disposed thereon), and the sample holder 120 (implemented at least in part in the example of FIG. 7 by a drawer 120A). The example of FIG. 7 includes two photodetectors, with one of the photodetectors corresponding to the test area 411 and another one of the photodetectors corresponding to the reference area 412. The PCB 110A and the PCB 415 are connected to be in signal communication with each other. The PCB 110A can be configured to perform DC/DC voltage regulation and so forth, as readily appreciated by one of ordinary skill in the art, given the teachings of the present invention provided herein.

Figure 8:
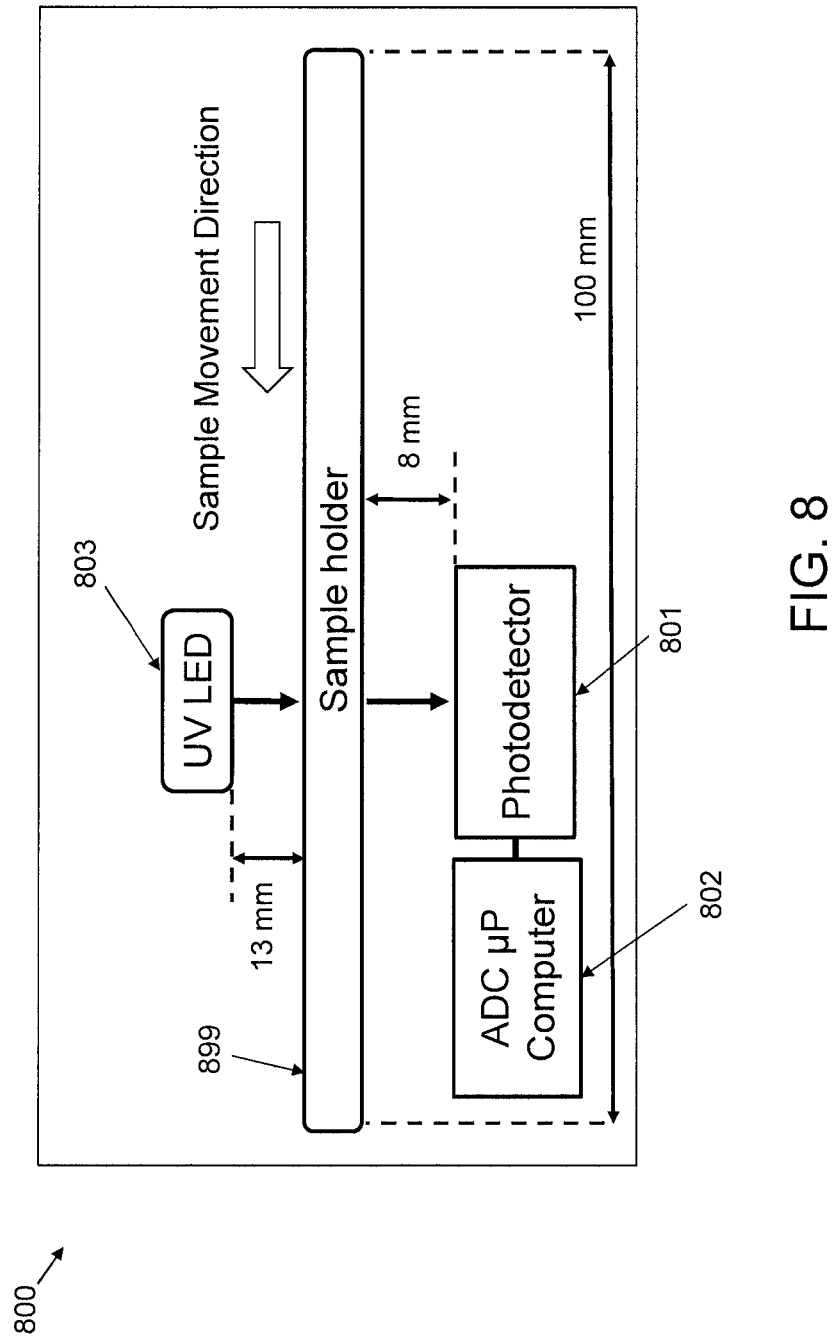
FIG. 8 shows a diagram of a lateral cross-sectional view of an implementation of part of the system of FIG. 1 in a transmission mode, in accordance with an embodiment of the present invention.
Figure 9:
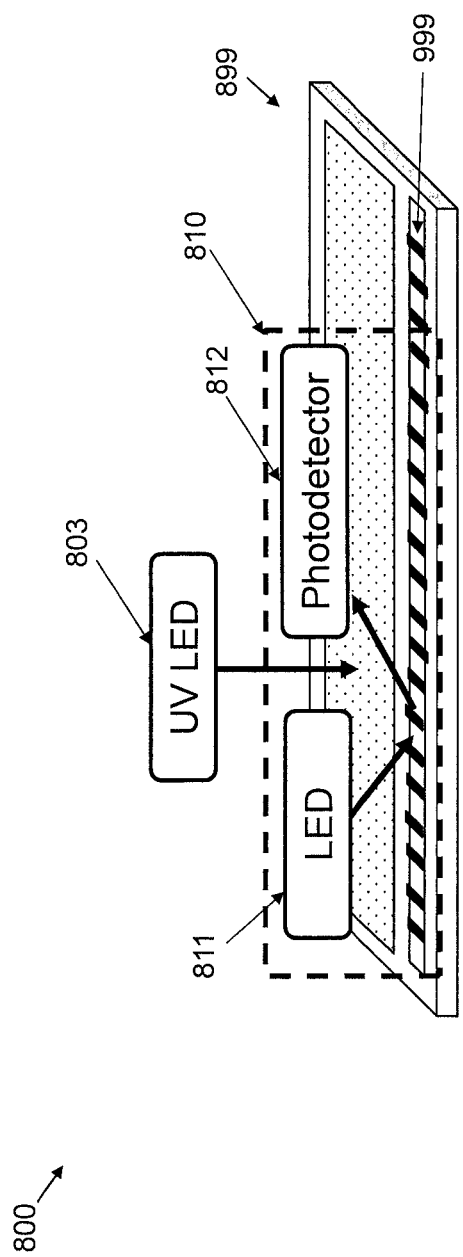
FIG. 9 shows a perspective view of the implementation of FIG. 8 in the transmission mode, in accordance with an embodiment of the present invention.
Figure 10:
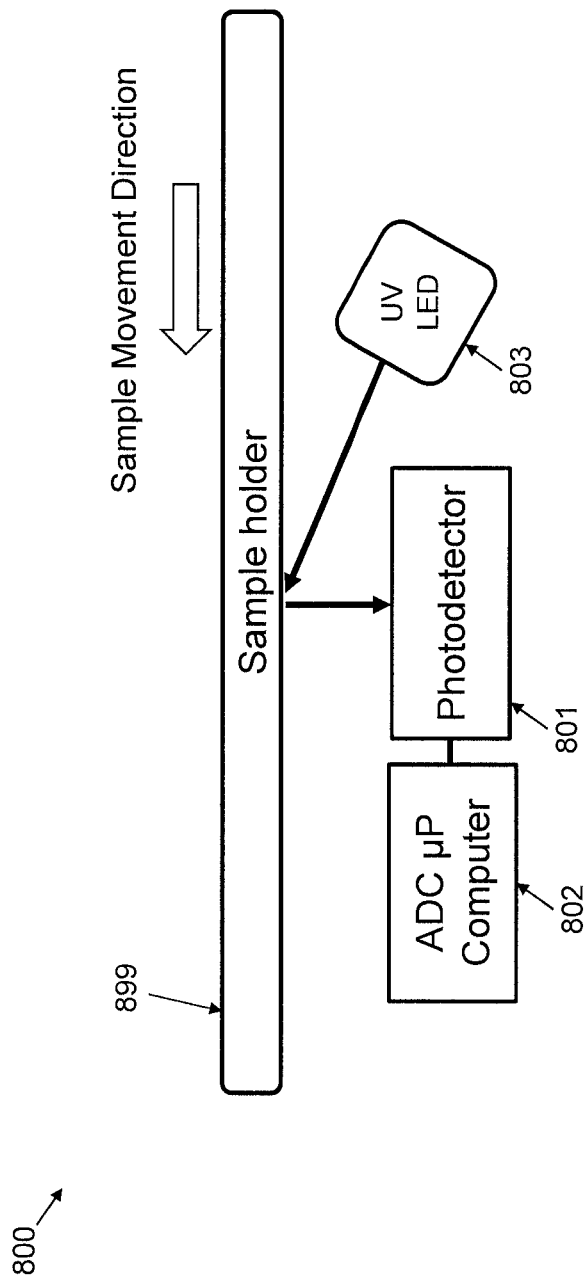
FIG. 10 shows a diagram of a lateral cross-sectional view of the implementation of FIG. 8 in a reflection mode.

FIG. 8 shows a lateral cross-sectional view of an implementation 800 of part of the system 100 of FIG. 1 in a transmission mode, in accordance with an embodiment of the present invention. FIG. 9 shows a perspective view of the implementation 800 of FIG. 8 in the transmission mode, in accordance with an embodiment of the present invention. FIG. 10 shows a lateral cross-sectional view of the implementation 800 of FIG. 8 in a reflection mode. Regarding the embodiments of FIGS. 8-10, the sample holder 120 of FIG. 1 is implemented by sample holder 899 in FIGS. 8-10.

In FIG. 8, implementation 800 demonstrates transmission analysis comprising a single photodetector 801 (connected to an Analog-to-Digital Converter (ADC) 802) and a UV LED 803 located on the same side of the sample holder 120. In FIG. 10, implementation 800 demonstrates reflection analysis comprising a single photodetector 801 (connected to an Analog-to-Digital Converter (ADC) 802) and a UV LED 803 located on the same side of the sample holder 120. In FIG. 9, the sample holder 899 is moved manually by the user (e.g., swiping), removing the need of an electrical motor or moving parts. The sample scanning location is controlled by a tracking system 810 (as shown in FIG. 9).

The tracking system 810, which includes a laser or LED operating at a certain wavelength (e.g., RED, although other colors can be used, as readily appreciated by one of ordinary skill in the art) 811 combined with a photodetector 812, reads the attached bar code 999 (see also FIG. 11) on the sample holder 899, obtaining the position reading along the sample length.

Figure 11:
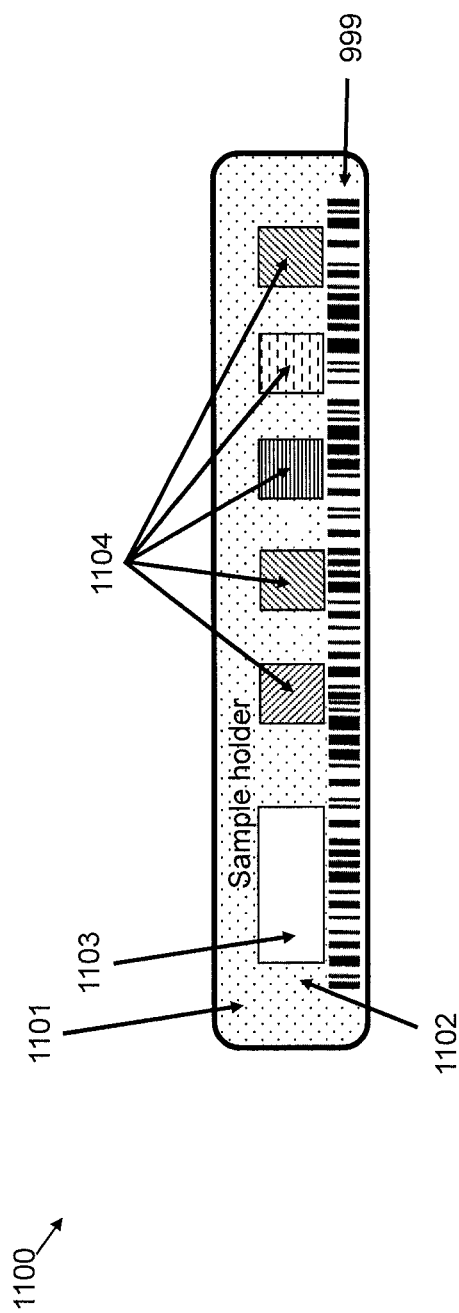
FIG. 11 shows a top view of an exemplary sample holder to which the present invention can be applied, in accordance with an embodiment of the present invention.

FIG. 11 shows a top view of an exemplary sample holder 1100 to which the present invention can be applied, in accordance with an embodiment of the present invention. The exemplary sample holder is particularly adapted to the implementation shown in FIG. 8 (that is, can be used to implement sample holder 899), and can also be applied with or without modification to the other embodiments and implementations shown herein.

In this embodiment, the sample holder 1100 is formed of a plastic carrier 1101 and includes the analytical parts 1102 (HT/HA, fluorescence marker, substrate substantially transparent to light emitted by a fluorescent marker).

Since the sample holder 1100 can be longer, it is possible to include a reference region 1103 and several liquid samples to be analyzed by different analysis regions 1104), using the same analysis substrate on the sample holder 1100.

The attached bar code 999 is present in the entire length of the samples on the sample holder 1100, allowing tracking of which region is being read/analyzed at a given time and also for sample identification.

Figure 12:
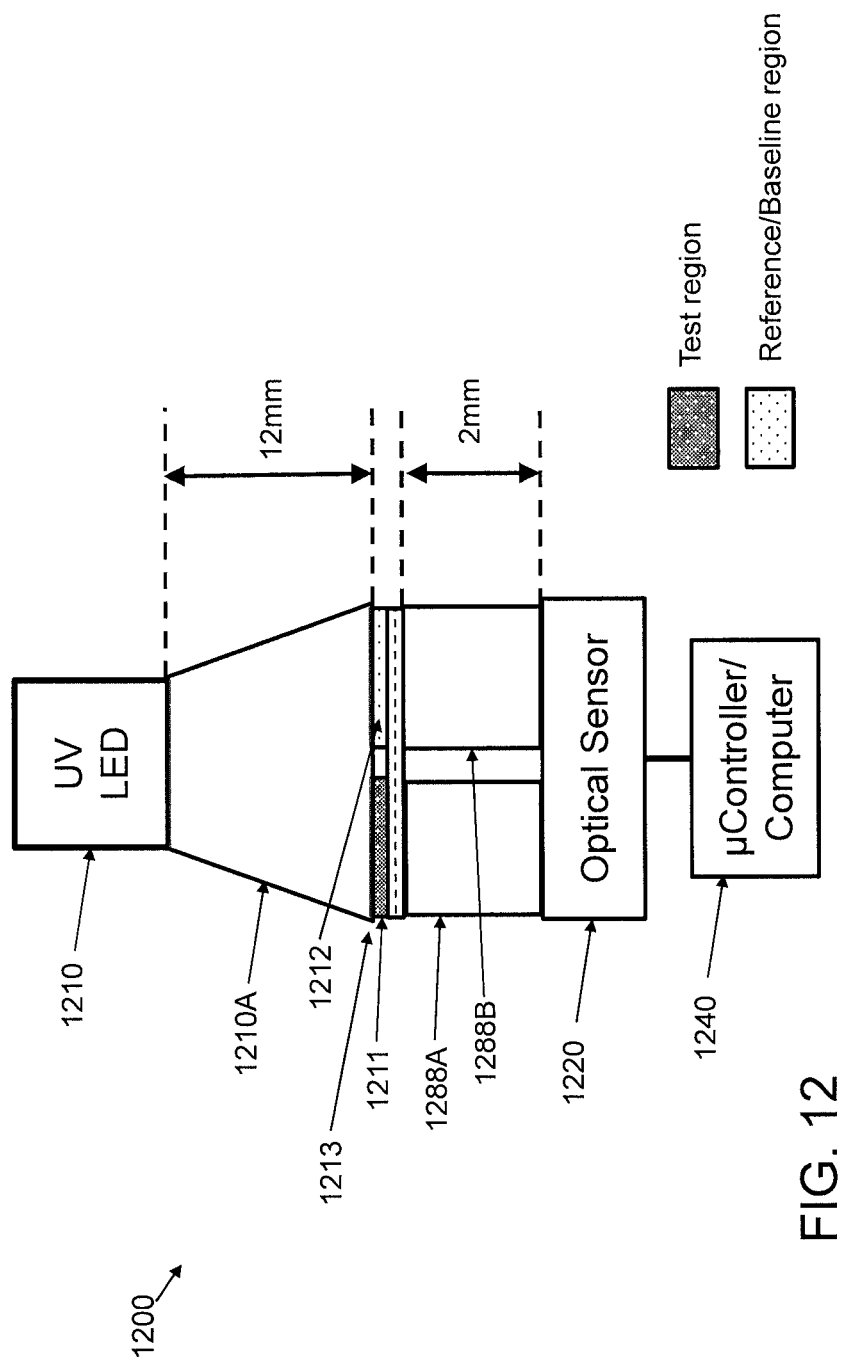
FIG. 12 shows another diagram of an implementation of part of the system of FIG. 1, in accordance with an embodiment of the present invention.

FIG. 12 shows another implementation 1200 of part of the system 100 of FIG. 1, in accordance with an embodiment of the present invention.

In implementation 1200, the presence and quantification of metal in a liquid sample is executed using image processing analysis, by using an optical sensor 1220 that can be implemented by any of a dedicated camera/CCD/CMOS sensor or a smartphone camera.

Hence, a UV light source (e.g., UV LED) 1210 provides UV light 1210A onto a test region 1211 and a reference region 1212 for an analysis substrate 1213. Radiation detected by the optical sensor 1220 is then processed by a microcontroller 1240. The radiation includes fluorescence signal 1288A generated from the test region 1211 and radiation 1288B passing through the reference region 1212.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with management effort or interaction with a provider of die service. This cloud model may include at least five characteristics, at least three service models, and at least four deployment models.

Characteristics are as follows:

On-demand self-service a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client, platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming, languages and tools supported by the provider. The consumer does, not manage or control the underlying cloud infrastructure including networks, servers, operating systems, or storage, hut has control over the deployed, applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and, lay exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud, computing environment is service oriented with a focus on statelessness, low coupling, modularity, and semantic interoperability. At the heart of cloud computing is an infrastructure that includes a network of interconnected nodes.

Figure 13:
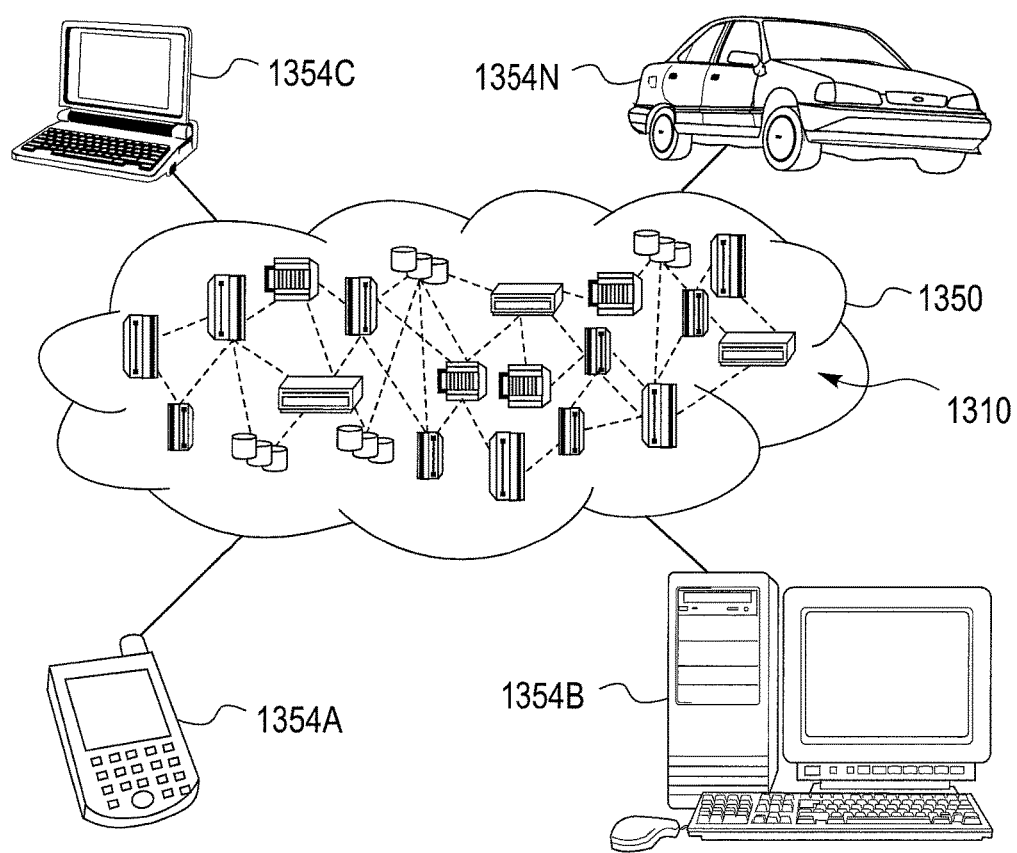
FIG. 13 shows a cloud computing environment, in accordance with, an embodiment of the present invention.

Referring now to FIG. 13, illustrative cloud computing environment 1350 is depicted. As shown, cloud computing environment 1350 includes one of more cloud computing nodes 1310 with which local computing devices used by cloud consumers, such as, for example, personal digital assistant (PDA) or cellular telephone 1354A, desktop computer 1354B, laptop computer 1354C, and/or automobile computer system 1354N may communicate. Nodes 1310 may communicate with one another. They may be grouped (not shown) physically or virtually, in one or more networks, such as Private, Community, Public, or Hybrid clouds as described hereinabove, or a combination thereof. This allows cloud computing environment 1350 to offer infrastructure, platforms and/or software as services for which a cloud consumer does not need to maintain resources on a local computing device. It is understood that the types of computing devices 1354A-N shown in FIG. 13 are intended to be illustrative only and that computing nodes 1310 and cloud computing environment 1350 can communicate with any type of computerized device over any type of network and/or network addressable connection (e.g., using a web browser.

Figure 14:
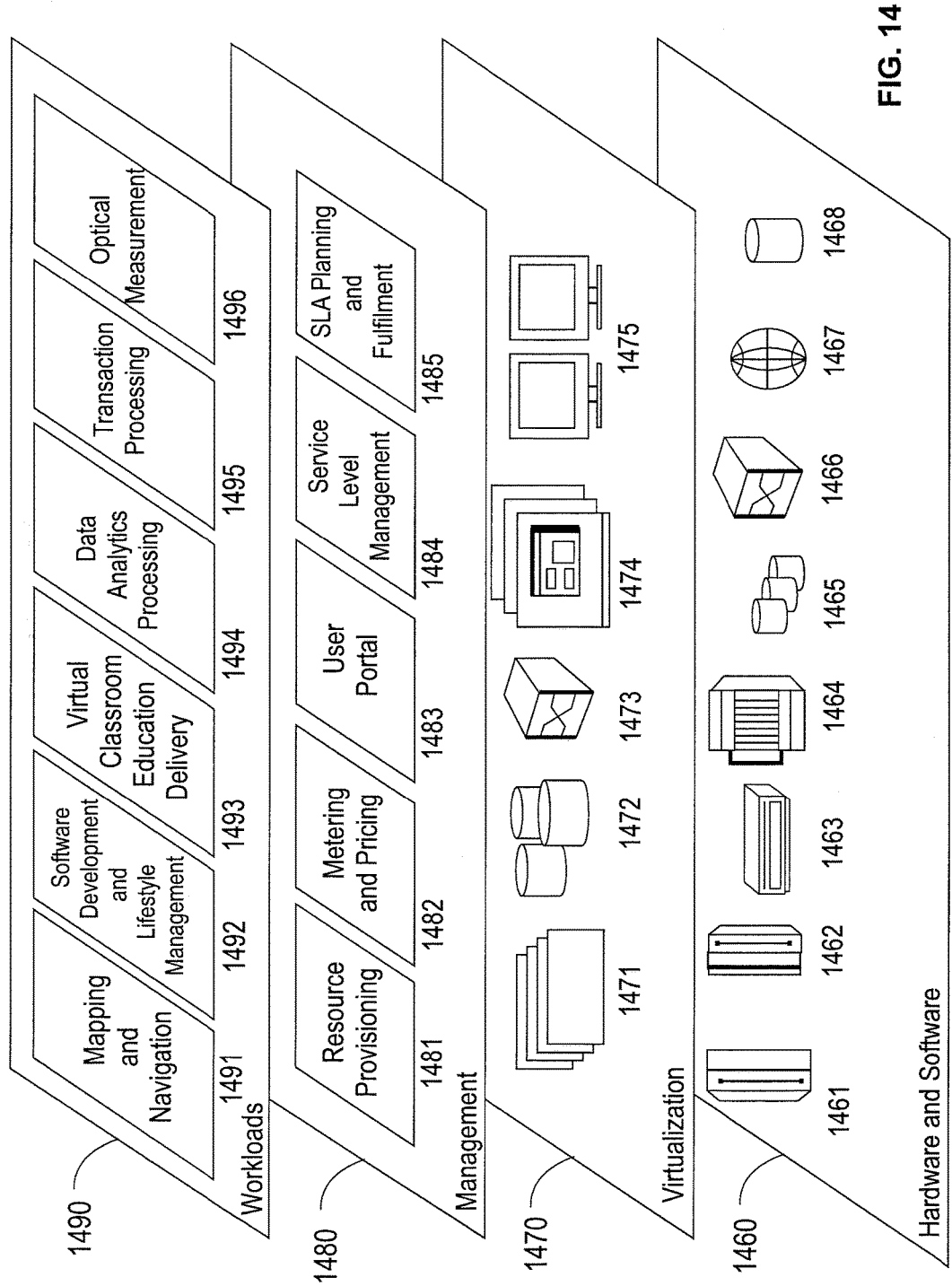
FIG. 14 shows abstraction model layers, in accordance with an embodiment of the present invention.

Referring now to FIG. 14, a set of functional abstraction layers provided by cloud computing environment 1350 (FIG. 13) is shown. It should be understood in advance that the components, layers, and functions shown in FIG. 14 are intended to be illustrative only and embodiments of the invention are not limited thereto. As depicted, the following layers and corresponding functions are provided:

Hardware and software layer 1460 includes hardware and software components. Examples of hardware components include: mainframes 1461; RISC (Reduced Instruction Set Computer) architecture based servers 1462; servers 1463; blade servers 1464; storage devices 1465; and networks and networking components 1466. In some embodiments, software components include, network application server software 1467 and database software 1468.

Virtualization layer 1470 provides an abstraction layer from which the following examples of virtual entities may be provided: virtual servers 1471; virtual storage 1472; virtual networks 1473, including virtual private networks; virtual applications and operating systems 1474; and virtual clients 1475.

In one example, management layer 1480 may provide the functions described below. Resource provisioning 1481 provides dynamic procurement of computing resources and other resources that are utilized to perform tasks within the cloud computing environment. Metering and Pricing 1482 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 1483 provides access to the cloud computing environment for consumers and system administrators. Service level management 1484 provides cloud computing resource allocation and management such that required service levels are met. Service Level Agreement (SLA) planning and fulfillment 1485 provide pre-arrangement for, and procurement of, cloud computing resources for which a future requirement is anticipated in accordance with an SLA.

Workloads layer 1490 provides examples of functionality for which the cloud computing environment may be utilized. Examples of workloads and functions which may be provided from this layer include: mapping and navigation 1491; software development and lifecycle management 1492; virtual classroom education delivery 1493; data analytics processing 1494; transaction processing 1495; and optical measurement 1496.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Reference in the specification to "one embodiment" or "an embodiment" of the present invention, as well as other variations thereof, means that a particular feature, structure, characteristic, and so forth described in connection with the embodiment is included in at least one embodiment of the present invention. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at, least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C).

This may be extended, as readily apparent by one of ordinary skill in this and related arts, for as many items listed.

Having described preferred embodiments of a system and method (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

The invention claimed is:

1. A portable optical measurement system for performing metal trace analysis on a liquid sample, the system comprising:
- a sample holder for holding an analysis substrate that includes a reference region and at least one test region co-planar with the reference region on the analysis substrate, the at least one test region including the liquid sample during the metal trace analysis, the reference region acting as a baseline, and the at least one test region testing a respective one of multiple liquid samples;
- an ultraviolet (UV) light source for emitting ultraviolet light illuminating the liquid sample;
- an optical sensor for detecting radiation emanating from the liquid sample and converting the detected radiation into an electrical signal;
- a microcontroller for processing the electrical signal; and
- an external interface for transmitting the processed electrical signal to an external device,
- wherein the analysis substrate is configured for manual movement by a user, the system further comprises a tracking system for detecting a sample scanning location for the metal trace analysis, wherein the tracking system comprises a light source, other than the UV light source, and another optical sensor, and wherein the other optical sensor detects light emitted by the light source.

2. The system of claim 1, wherein the UV light source comprises a printed circuit board and one or more UV light emitting diodes.

3. The system of claim 1, wherein the analysis substrate comprises a metal detection material, deposited over a UV transparent substrate, for receiving the liquid sample.

4. The system of claim 3, wherein an absorption or a reflection of the UV light through the metal detection material depends on a type and a concentration of the metal trace present in the liquid sample.

5. The system of claim 1, wherein the analysis substrate comprises a fluorescent indicator for converting the UV light emitted by the UV light source to another wavelength.

6. The system of claim 5, wherein the optical sensor detects variations in fluorescence intensity due to a presence of the metal trace in the liquid sample.

7. The system of claim 1, wherein the external interface transmits the processed electrical signal to a cloud service, and wherein the cloud service comprises a processor further processing the processed electrical signal for visualization of analysis results of the liquid sample.

8. The system of claim 1, wherein the external interface transmits the processed electrical signal to a cloud service, and wherein the cloud service comprises a processor further processing the processed electrical signal and sending a status signal that indicates the presence or the absence of the metal trace in the liquid sample.

9. The system of claim 1, further comprising a location device for providing or receiving location information designating where the liquid sample was collected.

10. The system of claim 1, further comprising a location device for providing or receiving location information designating where the liquid sample was analyzed.

11. The system of claim 1, further comprising an enclosure, and wherein the sample holder is movable and configured to slide into and out from the enclosure.

12. The system of claim 1, wherein the optical sensor comprises at least one photodetector configured to operate in a light transmission mode of the system and at least one other photodetector configured to operate in a light reflection mode of the system.

13. The system of claim 1, wherein the analysis substrate comprises a bar code disposed thereon.

14. The system of claim 13, wherein the at least one test region comprises multiple test regions, the multiple test regions testing the respective one of multiple liquid samples.

15. The system of claim 14, wherein the bar code includes respective portions, each corresponding to the respective one of the multiple testing areas for the multiple liquid samples, for allowing tracking of which of the multiple test areas is being analyzed at any given time and for sample identification.

16. The system of claim 13, wherein the analysis substrate further has a metal detection material and a fluorescent indicator disposed thereon.

17. A portable optical measurement system for performing metal trace analysis on a liquid sample, the system comprising:
- a sample holder for holding an analysis substrate comprising a metal detection material and fluorescent markers deposited over a UV transparent substrate, the analysis substrate including a reference region and at least one test region co-planar with the reference region on the analysis substrate, the at least one region including the liquid sample during the metal trace analysis, the reference region acting as a baseline, and the at least one test region testing a respective one of multiple liquid samples;
- an ultraviolet (UV) light source for emitting ultraviolet light illuminating the liquid sample;
- an optical sensor for detecting radiation emanating from the liquid sample and converting the detected radiation into an electrical signal;
- a microcontroller for processing the electrical signal;
- an external interface for transmitting the processed electrical signal to an external device to determine a presence or an absence of a metal trace in the liquid sample; and
- a communication indicator for receiving a communicated signal from the external device that indicates a status representative of the presence or the absence of the metal trace in the liquid sample, and for indicating the status to a user,
- wherein the analysis substrate is configured for manual movement by a user, the system further comprises a tracking system for detecting a sample scanning location for the metal trace analysis, wherein the tracking system comprises a light source, other than the UV light source, and another optical sensor, and wherein the other optical sensor detects light emitted by the light source.

* * * * *